United States Patent [19]

Kollerup

[11] Patent Number: 5,718,696

[45] Date of Patent: Feb. 17, 1998

[54] OSTOMY APPLIANCE

[75] Inventor: Ib Kollerup, Espergærde, Denmark

[73] Assignee: Coloplast A/S, Denmark

[21] Appl. No.: 704,502

[22] PCT Filed: Mar. 10, 1995

[86] PCT No.: PCT/DK95/00114

§ 371 Date: Sep. 24, 1996

§ 102(e) Date: Sep. 24, 1996

[87] PCT Pub. No.: WO95/24169

PCT Pub. Date: Sep. 14, 1995

[30] Foreign Application Priority Data

Mar. 11, 1994 [DK] Denmark .................. 0289/94

[51] Int. Cl.$^6$ ........................... A61F 5/44
[52] U.S. Cl. .............. 604/339; 604/332; 604/338; 604/344
[58] Field of Search ............... 604/332, 339, 604/338, 342, 344

[56] References Cited

U.S. PATENT DOCUMENTS 4,834,731  5/1989  Nowak et al. .
4,973,323  11/1990 Kaczmarek et al. .
5,185,008  2/1993  Lavender ................ 604/342
5,330,454  7/1994  Klingler et al. .

FOREIGN PATENT DOCUMENTS 0416397  3/1991  European Pat. Off. .
9304646  3/1993  WIPO .

*Primary Examiner*—Robert A. Clarke
*Attorney, Agent, or Firm*—Ostrolenk, Faber, Gerb & Soffen, LLP

[57] ABSTRACT

An ostomy appliance is a convex product where a layer of adhesive is present to the convex side of the product. The adhesive is present on a thermoplastic carrier sheet disposed between the adhesive and a ring-shaped body having a convex proximal side, and the carrier sheet is attached, e.g. by welding, to the ring-shaped body along the inner periphery and the outer periphery thereof. At its peripheral, plane part, the appliance has a plane layer of a thermostable material, such as paper, in close connection with the adhesive. The thermostable material extends radially outside the outer periphery of the ring-shaped body and provides stability during thermoforming.

10 Claims, 4 Drawing Sheets

OSTOMY APPLIANCE

This is a 371 of PCT/DK/00114 filed Mar. 10, 1995.

BACKGROUND OF THE INVENTION

The invention concerns an ostomy appliance whose proximal side has a convex face which is provided with adhesive by means of which the ostomy appliance can be adhered to the skin of a user, and whose distal side carries a collection bag or a coupling part therefor.

Below an ostomy patient or an ostomist denotes a person having a colostomy, an ileostomy or a urostomy. In such persons the colon, the ileum or the ureter has been exposed surgically such that the waste products of the body, which are conveyed through these organs, are discharged through an artificial opening and are collected in a collection bag, which is ordinarily adhered to the skin by means of an adhesive plate with an opening surrounding the stoma.

It is frequently seen in ostomy patients that the closest surroundings of the stoma, at a distance of 1–2 cm, are recessed or are positioned in a crater or a cavity with respect to the rest of the skin surface that surrounds the stoma. For such patients it is expedient to use an ostomy product where the adhesive surface around its opening for receiving the stoma has a part which is convex and protrudes toward the user with a view to enabling the adhesive face of the ostomy appliance to engage and adhere to the skin everywhere in the crater or the cavity. In particular, it is important that the ostomy appliance adheres well to the skin as closely to the stoma as possible, and this location is most frequently the one lying deepest. The shape of the forwardly protruding part of the adhesive face may e.g. be domed or conical, and such products are known under the designation convex products. Throughout the specification the term convex has this broad meaning irrespective of the actual embodiment. EP 317 326 describes a convex product where a rigid ring, on its entire convex side, carries an intermediate ring of a soft thermoplastic foam adhered to the rigid ring. The intermediate ring carries a layer of adhesive to position the product on the skin of a user. The foam ring is a cost-adding component, and the attachment by gluing to the rigid ring adds to the cost of the manufacturing process.

WO 93/04646 and EP 416 397 describe convex products where a layer of adhesive suitable for use on the human skin is arranged directly on the convex face of a ring-shaped body. In these convex products the convex shape of the adhesive is given by the convex shape of the ring-shaped body, and the adhesive has no possibility of adapting its shape to the user's shape around the stoma. Accordingly, air pockets may occur, which causes deficient adhesion to the user's skin.

DESCRIPTION OF THE INVENTION

With an ostomy appliance comprising a ring shaped body having a convex proximal side and a distal side and as well as an inner periphery and an outer periphery, and a layer of adhesive to attach the ring-shaped body to a user's skin with the proximal side facing the user's skin, which is characterized in that the adhesive is present on a thermoplastic carrier sheet having at least the same extent as the adhesive, and that the carrier sheet is disposed between the adhesive and the ring-shaped body and is attached to the proximal side of the ring-shaped body along the inner periphery and the outer periphery thereof with mutual spaces. The layer of adhesive is not firmly connected to the ring-shaped body over the entire convex face of the body, but can move with respect to the body. The layer of adhesive is hereby able to follow irregularities in the skin around the user's stoma and to adhere completely to the skin without air pockets. This ensures a more stable adhesion of the ostomy appliance to the user's skin.

The production of ostomy products with a flat proximal adhesive side includes producing a plane disc of adhesive suitable for use on the human skin which is provided with a plastics sheet on both sides. The plastics sheet on the distal side of the adhesive is attached, e.g. by gluing or welding, to a collection bag or to a coupling part, to which a collection may be detachably coupled. The sheet on the proximal side of the adhesive is a protective sheet, which is removed prior to use, and the ostomy appliance is then adhered to the user's skin by means of the substantially plane proximal side of the adhesive. Plane discs of adhesive having a carrier sheet and a protective sheet of the above-mentioned type may advantageously also be used for the production of ostomy appliances of the present type, viz. convex products, since the disc of adhesive material having a carrier sheet and a protective sheet may be thermoformed to assume the convex shape. Then, the carrier sheet may advantageously be attached to the ring-shaped body, as stated in claim 2. The provision of air access to the space between the ring-shaped body and the carrier sheet makes it possible to provide an even considerable distance between the ring-shaped body and the carrier sheet, so that the adhesive is able to follow considerable irregularities in the user's skin.

Thermoforming of the above-mentioned adhesive disc with a carrier sheet and a protective sheet to a convex product involves the risk that the thermoplastic sheets when cooled will retract anisotropically with the result that the adhesive disc does not assume the desired plane shape, but gets wrinkles and bulges. This may cause poor adhesion to the user's skin. With an ostomy appliance as stated in claim 4, the plane layer of thermostable material ensures that such inexpedient bulges and wrinkles are avoided. Consequently, it will be possible for the adhesive to follow possible irregularities in the user's skin to a much greater degree.

BRIEF DESCRIPTION OF THE DRAWINGS

A preferred embodiment of the invention will be explained below with reference to the drawing, in which.

DETAILED DESCRIPTION OF THE DRAWINGS

Figure 1:
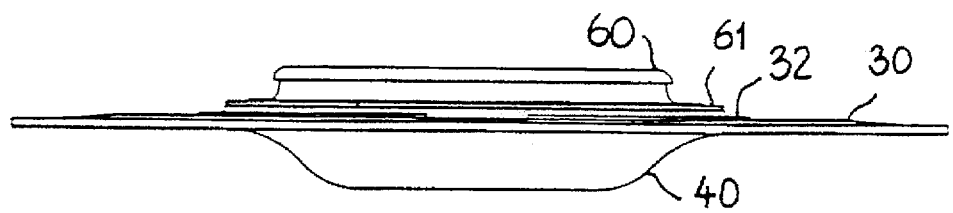
FIG. 1 is a lateral view of an ostomy product having a coupling part to which a collection bag may be attached.
Figure 2:
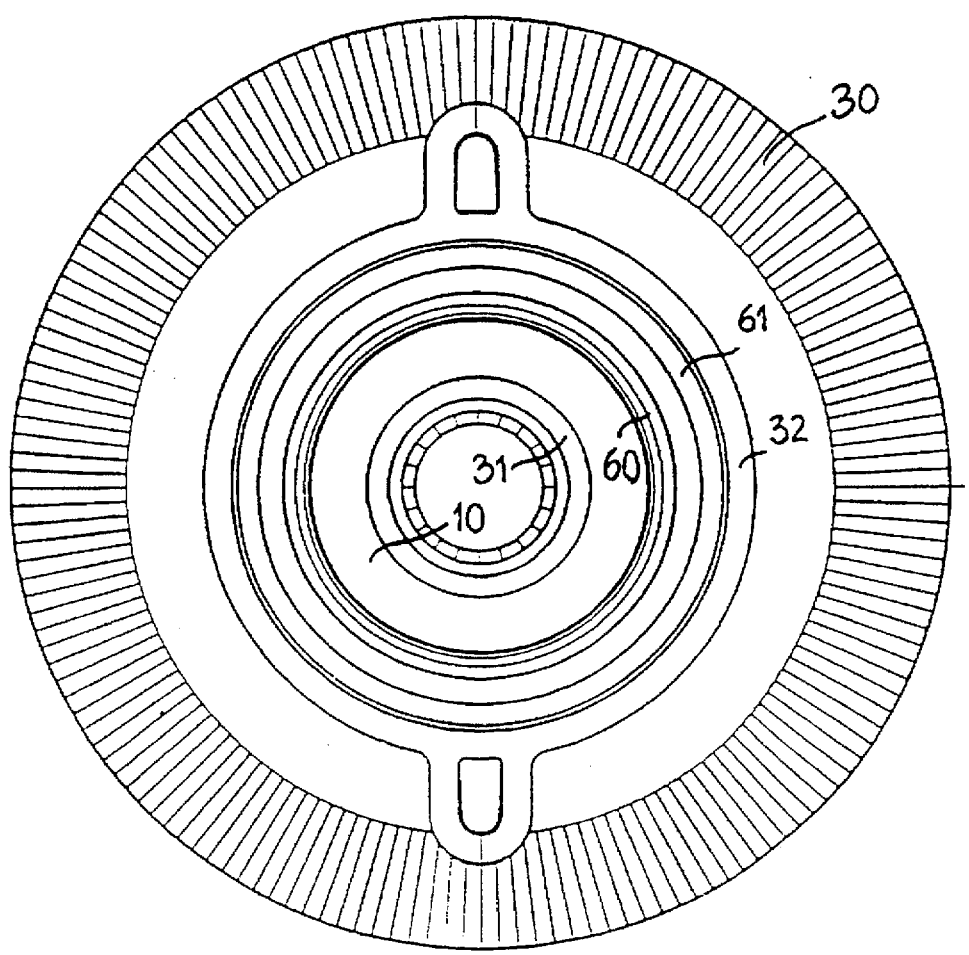
FIG. 2 shows the distal side of the ostomy product of FIG. 1.
Figure 3:
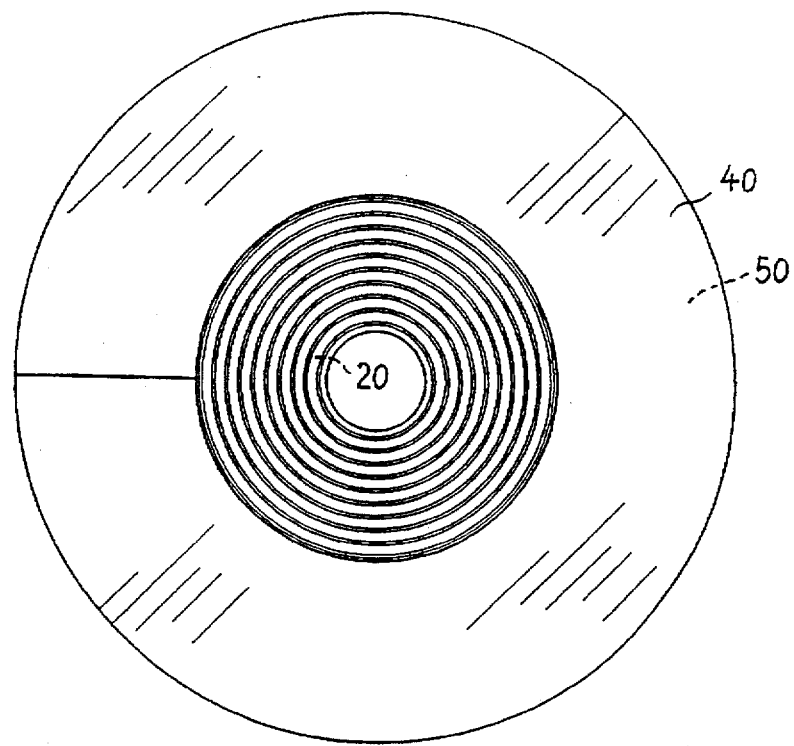
FIG. 3 shows the proximal side of the ostomy product of FIG. 1.
Figure 4:
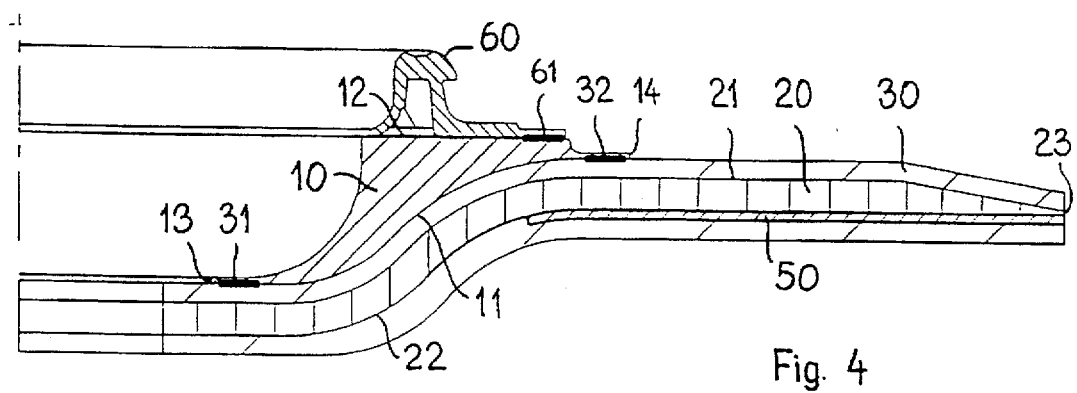
FIG. 4 shows an axial section through the ostomy product of FIG. 1.
Figure 5:
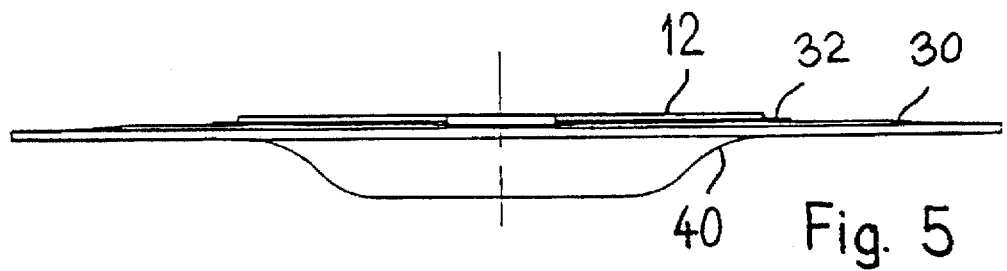
FIG. 5 is a lateral view of an ostomy product like in FIG. 1, but without a coupling part.
Figure 6:
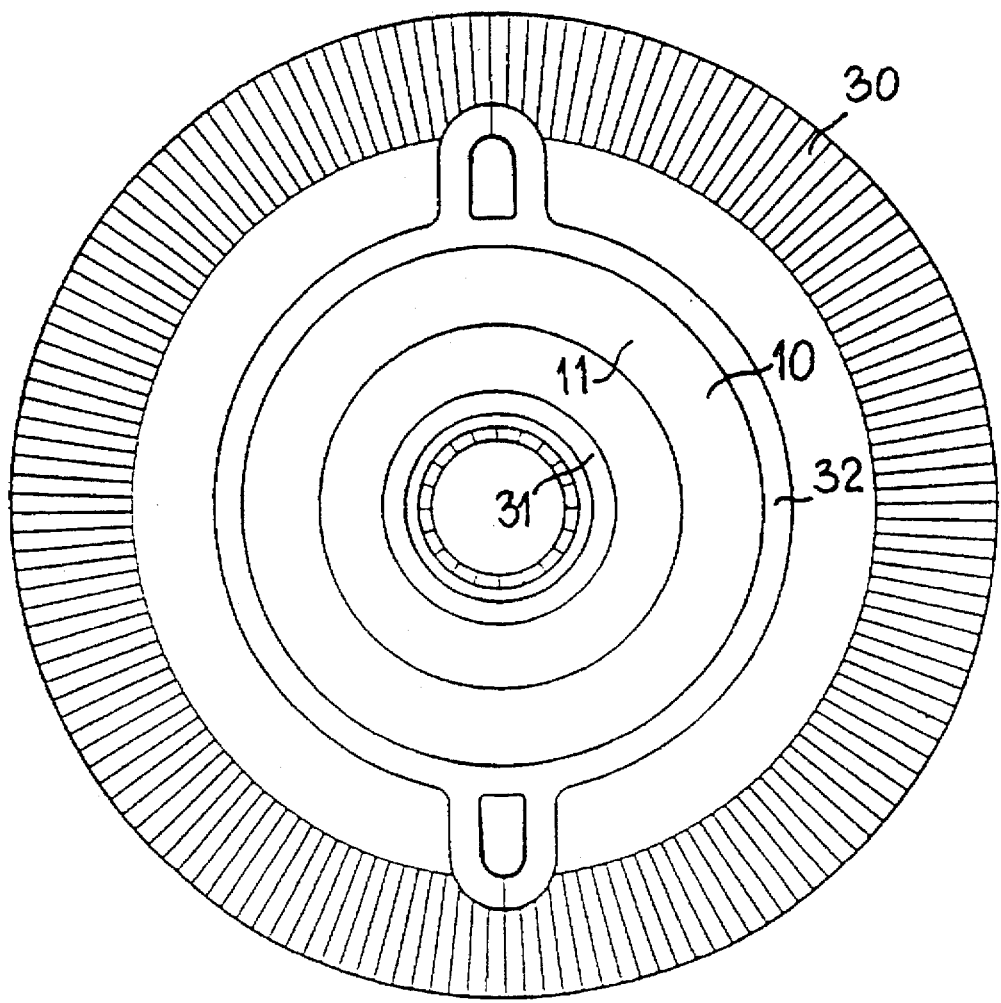
FIG. 6 shows the distal side of the ostomy product of FIG. 5.

The ostomy product of FIGS. 1–4 and the ostomy product of FIGS. 5–6 have many technical features in common, which have therefore been given the same reference numerals.

FIG. 4 shows a ring-shaped body 10 made of a plastics type which is flexible and relatively rigid so that it is substantially dimensionally stable under normally occurring loads. The ring-shaped body 10 has a proximal side 11 which is convex, and which forms an S-shaped curve in the shown axial section. Further, the ring-shaped body 10 has a distal side 12 which is plane in the shown embodiment, but the distal side 12 may have other shapes according to the purpose.

A layer 20 of adhesive has the shape of a circular ring disc and consists of an adhesive suitable for use on the human skin which is capable of adhering to the skin of a human over an extended period of time. On its distal side 21 the layer of adhesive 20 adheres to a thermoplastic carrier sheet 30, which has substantially the same extent in a radial direction as the adhesive 20. FIG. 4 shows the carrier sheet 30 with the adhesive 20 disposed quite close to the convex proximal side 11 of the ring-shaped body 10, and the carrier sheet 30 is welded to the ring-shaped body 10 along the inner periphery 13 and outer periphery 14 thereof at respective welded seams 31, 32. The welded seam 31 at the inner periphery 13 of the ring-shaped body has the shape of a closed ring and thus forms a completely tight seal between the ring-shaped body 10 and the carrier sheet 30. The welded seam 32 at the outer periphery 14 of the ring-shaped body 10 is likewise ring-shaped, but is interrupted at least at one place, thereby providing for air access, at the outer periphery 14, through the welded seam 32 to the space between the convex, proximal side 11 of the ring-shaped body and the carrier sheet 30. On its proximal side the layer of adhesive 20 has a protective sheet 40 of a thermoplastic material which has been siliconized on its distal side facing the layer 20 of adhesive, so that the protective sheet 40 can easily be released and be removed from the layer 20 of adhesive prior to use.

A substantially plane layer 50 of paper or another thermostable material is disposed in close connection with the adhesive 20 and extends from the outer periphery 23 thereof and covers the entire plane part of the adhesive 20, said paper layer 50 extending past and further inwards than the outer periphery 14 of the ring-shaped body 10. This stabilizes the welded seam 32. The expression thermostable means in this context that the paper layer 50 is stable at the temperatures which are used in the thermoforming of the carrier sheet 30 and the protective sheet 40, between which the adhesive 20 is disposed.

In the production of the ostomy product of FIGS. 1–4 the starting material is the ring-shaped body 10 and a plane, composite plate in the shape of a circular ring disc consisting of the layer 20 of adhesive with the carrier sheet 30, the protective sheet 40 and the paper 50, which have been treated with a release agent, e.g. siliconized on the side facing the layer of adhesive 20. At least the central part of this composite disc is heated, said central part being positioned within a radius corresponding to the outer periphery 14 of the ring-shaped body 10, since this central part is to be deformed so that it assumes the cross-section shown in FIG. 4. Heating is effected to a temperature at which the adhesive 20, the carrier sheet 30 and the protective sheet 40 become plastic, and deformation can take place by vacuum forming or by pressing together the plastic central part of the disc and the ring-shaped body 10 in another manner to cause the desired deformation of the disc. Then the two ring-shaped welded seams 31 and 32 are made along the inner periphery 13 and the outer periphery 14, respectively, of the ring-shaped body 10. Alternatively, the attachment may take place by gluing. In the subsequent cooling, the thermoplastic materials tend to curl or wrinkle because of an anisotropic contraction, but owing to the presence of the thermostable layer 50, such bulges, wrinkles or curls cannot occur, because the thermostable layer of paper is dimensionally stable against the changes in temperature occurring here.

The distal side 12 of the ring-shaped body 10 is plane here, and a coupling part 60 is attached to the distal side 12 of the ring-shaped body 10 at a ring-shaped welded seam 61. The coupling part 60 is adapted to be coupled to a collection bag of the ostomy appliance in a known manner. The embodiment of FIGS. 5 and 6 corresponds to the embodiment of FIGS. 1–4, except that there is no coupling part here. This embodiment is adhered with its proximal side to the user's skin and thus forms a substantially plane distal face on which an ostomy product having a plane proximal adhesive face may be attached by adhesion.

Figures 7, 8:
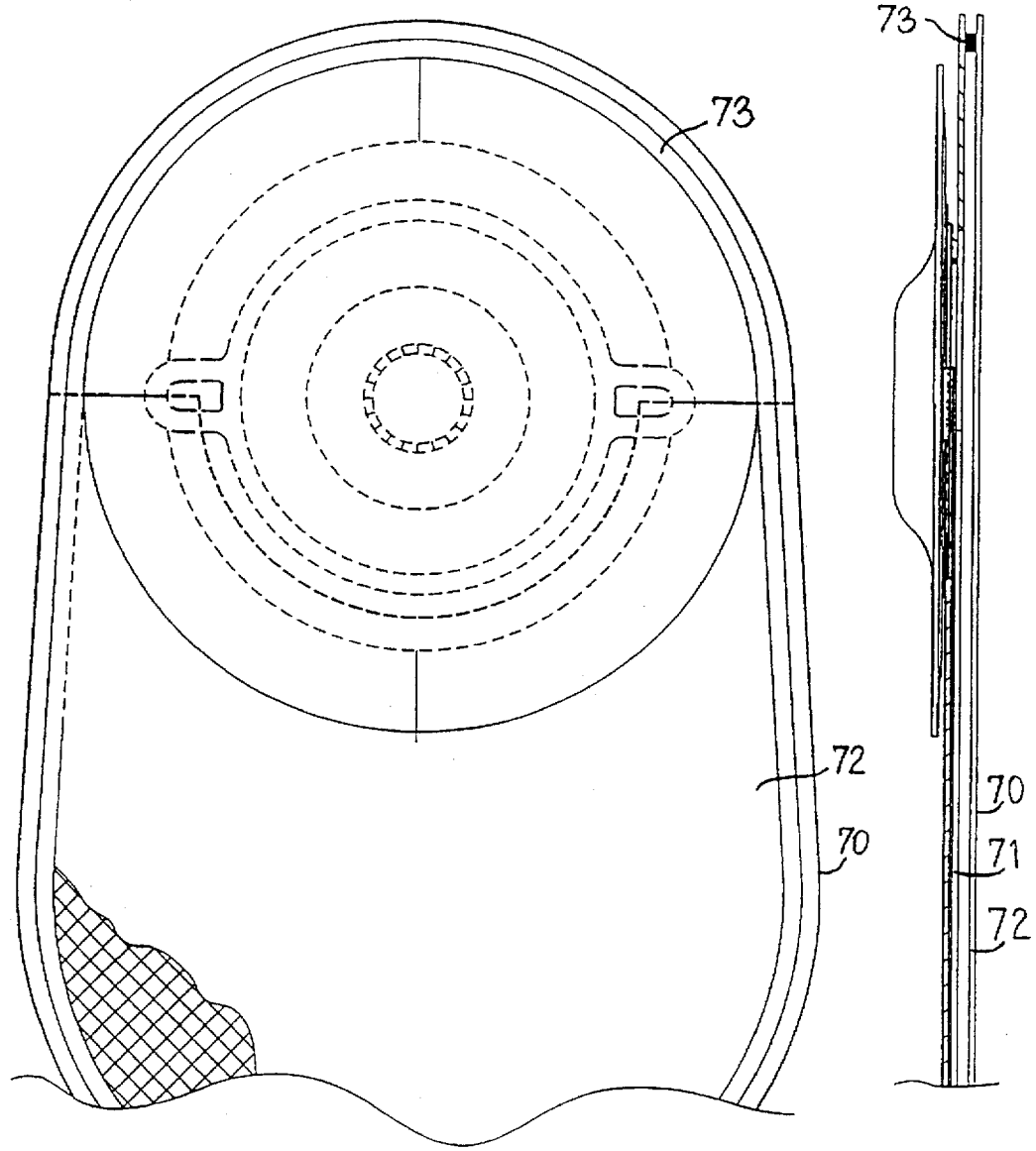
FIG. 7 is a lateral view of an ostomy product according to the invention with a fixedly mounted collection bag.
FIG. 8 shows the distal side of the ostomy product of FIG. 7.

FIGS. 7 and 8 show the ostomy product of FIGS. 5–6 with a collection bag 70 attached by gluing or welding to the distal side 12 of the ring-shaped body 10. The collection bag 70 consists of a proximal sheet member 71 and a distal sheet member 72 which are welded together at a welded seam 73 along their peripheries. The collection bag 70 has an inlet opening in a known manner, which is essentially coaxial with the central opening in the ring-shaped body 10.

When the ostomy appliance of FIGS. 1–4, FIGS. 5–6 or FIGS. 7–8 is to be used, both the protective sheet 40 and the paper 50 are removed, thereby exposing the proximal side 22 of the adhesive layer 20, and the ostomy appliance is then adhered to the user's skin such that the appliance is centered around the user's stoma.

I claim:

1. An ostomy appliance comprising
a ring shaped body having a convex proximal side a distal side, an inner periphery and an outer periphery,
a thermoplastic carrier sheet having a boundary and a first side and a second side, said first side being attached to said proximal side of said ring shaped body along said inner periphery and along said outer periphery with a space therebetween,
a layer of adhesive on said second side of said thermoplastic carrier sheet, said layer of adhesive being within said boundary, for attaching the appliance to a user's skin.

2. The ostomy appliance according to claim 1, wherein said carrier sheet is attached to the ring-shaped body at a non-closed ring shaped welded seam along the outer periphery, thereby providing air access to the space.

3. The ostomy appliance according to claim 1, wherein said carrier sheet is attached to the ring-shaped body at a closed ring-shaped welded seam along the inner periphery.

4. The ostomy appliance according to claim 1, wherein said carrier sheet is thermoplastic and extends considerably beyond the outer periphery of the ring-shaped body, where the carrier sheet is essentially plane.

5. The ostomy appliance according to claim 4, wherein it comprises a thermoplastic protective sheet which covers the proximal side of the adhesive, and which has release properties with respect to the adhesive.

6. The ostomy appliance according to claim 4 wherein, it comprises a plane layer of a thermostable material which is in close connection with the adhesive, and which extends radically inwards substantially from the outer periphery of the adhesive and overlaps the outer periphery of the ring-shaped body.

7. The ostomy appliance according to claim 6 wherein said thermostable material is disposed on the proximal side of the adhesive and has release properties with respect to the adhesive.

8. The ostomy appliance according to claim 7, wherein said thermostable material is siliconized paper.

9. The ostomy appliance according to claim 1, wherein said distal side of the ring-shaped body is attached to a collection bag.

10. The ostomy appliance according to claim 1, wherein said distal side of the ring-shaped body has coupling means to releasably attach a collection bag.

* * * * *